United States Patent [19]
Alexon et al.

[11] Patent Number: 5,080,983
[45] Date of Patent: Jan. 14, 1992

[54] BATTERY

[75] Inventors: Charles E. Alexon, Amery, Wis.; Matthew T. Scholz, Woodbury; Robert P. Zaspel, St. Paul, both of Minn.

[73] Assignee: Minnesota Mining and Manufacturing Company, St. Paul, Minn.

[21] Appl. No.: 568,602

[22] Filed: Aug. 16, 1990

[51] Int. Cl.$^5$ .................. H02J 7/00; H01M 10/02
[52] U.S. Cl. ........................... 429/54; 310/50; 318/139; 429/57; 429/72; 429/163
[58] Field of Search .......... 429/54, 57, 72, 163; 320/2; 310/50; 318/139

[56] References Cited

U.S. PATENT DOCUMENTS

| | | | |
|---|---|---|---|
| 2,132,224 | 10/1938 | Snyder | 251/147 |
| 3,120,845 | 2/1984 | Horner | 128/310 |
| 3,173,417 | 3/1965 | Horner | 128/305 |
| 3,497,104 | 2/1970 | White | 220/44 |
| 3,497,396 | 2/1970 | Goodwin | 136/179 |
| 3,734,207 | 5/1973 | Fishbein | 173/163 |
| 3,909,302 | 9/1975 | Mermelstein | 136/177 |
| 4,091,880 | 5/1978 | Troutner et al. | 173/163 |
| 4,447,508 | 5/1984 | Jensen | 429/57 |
| 4,584,248 | 4/1986 | Iwata | 429/54 |
| 4,636,446 | 1/1987 | Lee | 429/54 |
| 4,728,876 | 3/1988 | Mongeon et al. | 320/2 |
| 4,892,794 | 1/1990 | Scholz | 429/72 |

FOREIGN PATENT DOCUMENTS 0238204  9/1987  European Pat. Off. .

OTHER PUBLICATIONS

NASA Tech Brief, Electrolyte Reservoir Would Lengthen Cell Life.
M. Evans, Manual of Model Steam Locomotive Const. pp. 129-130 (London, 1960).
Stryker Surgical "Maintenance Manual & Operating Instructions".
Stryker trade literature.
Dyonics trade literature.
AATCC Test Method 118-1983 Oil Repellency: Hydrocarbon Res. Test 61 AATCC Manual.
Surface Tension of Methyl Alcohol in Water, CRC Handbook of Chemistry and Physics F-34 (69th Ed., 1988) Solutions, Engineering New Ideas in Plastics (Porex Tech., Fairburn, Georgia, 1989).

*Primary Examiner*—Asok Pal
*Attorney, Agent, or Firm*—Gary L. Griswold; Walter N. Kirn; Stephen W. Bauer

[57] ABSTRACT

A battery including a vent tower extending inwardly into the battery cell and terminating at a free end. A passageway is provided through the vent tower to allow the venting of gas. The vent tower includes a porous, hydrophobic filter in the passageway adjacent the free end of the vent tower, and a pressure-relief valve in the passage. The free end of the vent tower is spaced sufficiently from any wall of the battery casing that any void defined by a horizontal plane along the free end of the vent tower and the walls of the casing below the horizontal plane is greater than the volume of free electrolyte regardless of the orientation of the battery.

20 Claims, 2 Drawing Sheets

BATTERY

The invention relates generally to batteries, more particularly to a vented battery that is adapted to withstand high temperatures, such as generated during heat and/or steam sterilization in an autoclave, with minimal loss of electrolyte and that is designed for powering orthopedic surgical instruments.

BACKGROUND OF THE INVENTION

Batteries that are designed to withstand high temperatures, e.g., 270 degrees Fahrenheit (132 degrees Celsius), are typically vented to permit gas to escape and prevent excessive pressure in the battery. Battery vents, however, may permit electrolyte to escape when the battery is held with the vent below the level of the electrolyte, such as frequently occurs if the battery is attached to a hand-held powered device. Electrolyte may also escape during heat-sterilization if the battery is carelessly placed in an autoclave with the vent below the level of the electrolyte.

One approach for reducing the loss of electrolyte is to place a pressure-relief valve in the vent. Such a valve allows gas to be vented and reduces loss of electrolyte in normal operation, but does not prevent the discharge of electrolyte when the pressure in the battery is sufficient to open the relief valve. As a result of the gradual or sudden loss of electrolyte through a vent, the operation of vented batteries has been impaired before their components have worn out.

These problems with vented batteries have been particularly troublesome when the batteries are used to power orthopedic or other surgical instruments, which generally require high power and a high degree of reliability. These batteries are usually heat sterilized between each use, and have sufficient capacity to power the instrument during a potentially complicated and time-consuming surgical operation. It is especially important that sufficient electrolyte be retained to completely wet the electrodes throughout the life of the battery. Free or "excess" electrolyte is desirable in new batteries because electrolyte is typically lost as hydrogen and oxygen during charging of the battery. In addition, it is unacceptable for electrolyte to leak from the battery during a surgical operation.

Coassigned U.S. Pat. Nos. 4,728,876 and 4,892,794 describe orthopedic drive assemblies including a silver/zinc battery having potassium hydroxide electrolyte, and a vent assembly for venting gas from the battery cell. Those vent assemblies include a spring-biased ball valve in a vent passageway, and a curtain of hydrophobic polymeric material (e.g., polytetrafluoroethylene) across the passageway. U.S. Pat. Nos. 3,120,845; 3,173,417; 3,734,207; and 4,091,880 describe other battery-powered surgical instruments.

U.S. Pat. No. 3,909,302 discloses a vent cap for liquid acid batteries including a hydrophobic diaphragm (e.g., a microporous polytetrafluoroethylene sheet) across a vent passageway. U.S. Pat. Nos. 2,132,224; 3,497,104; 3,497,396; 4,584,248; and 4,636,446 disclose various battery vents or valves.

SUMMARY OF THE INVENTION

The present invention provides a battery that is adapted to withstand high temperatures, such as generated during heat or steam sterilization in an autoclave, with minimal loss of electrolyte and that is designed for powering various portable powered devices, such as orthopedic surgical instruments, which are typically operated in many different orientations.

Generally, a battery of the invention comprises a casing having walls defining at least one battery cell, with aqueous fluid electrolyte in the cell, and an electrode assembly in the cell including positive and negative electrodes normally immersed in the electrolyte. The battery further includes a vent tower extending inwardly from a wall of the casing into the cell and terminating at a free end, with a passageway opening inwardly through the free end of the vent tower and opening outwardly through the casing for venting gases and pressure from the cell. A porous, hydrophobic filter is provided in the passageway adjacent the free end of the vent tower permitting movement of gas through the passageway while restricting movement of liquid through the passageway. Pressure-relief means is also provided in the passageway for allowing gas in the cell above a predetermined pressure to escape through the passageway while sealing the passageway against the escape of gas below the predetermined pressure. The free end of the vent tower is spaced sufficiently from any wall defining the battery cell that any void defined by a horizontal plane along the free end of the vent tower and the walls of the casing below the horizontal plane is greater than the volume of free electrolyte regardless of the orientation of the battery.

Preferably, the free end of the vent tower is configured so as to facilitate movement of electrolyte away from the passageway. For example, the free end of the vent tower may have a generally conical, frustoconical or hemispherical configuration, with the surface of the free end generally sloping away from the passageway to facilitate movement of electrolyte away from the passageway. Most preferably, the filter has an inner end portion adjacent the free end of the vent tower, and this inner end portion has a generally conical, frustoconical or hemispherical end surface extending slightly outwardly from the free end of the vent tower to facilitate movement of electrolyte away from the passageway.

Other features will be in part apparent and in part pointed out hereinafter.

BRIEF DESCRIPTION OF THE DRAWING

The invention will be further described with reference to the drawing wherein corresponding reference numerals indicate corresponding parts throughout the several views of the drawing, and wherein:

FIG. 3 is a further enlarged cross-sectional view of a portion of the battery of FIG. 2, showing a vent tower of the invention.

DETAILED DESCRIPTION OF A PREFERRED EMBODIMENT

Figure 1:
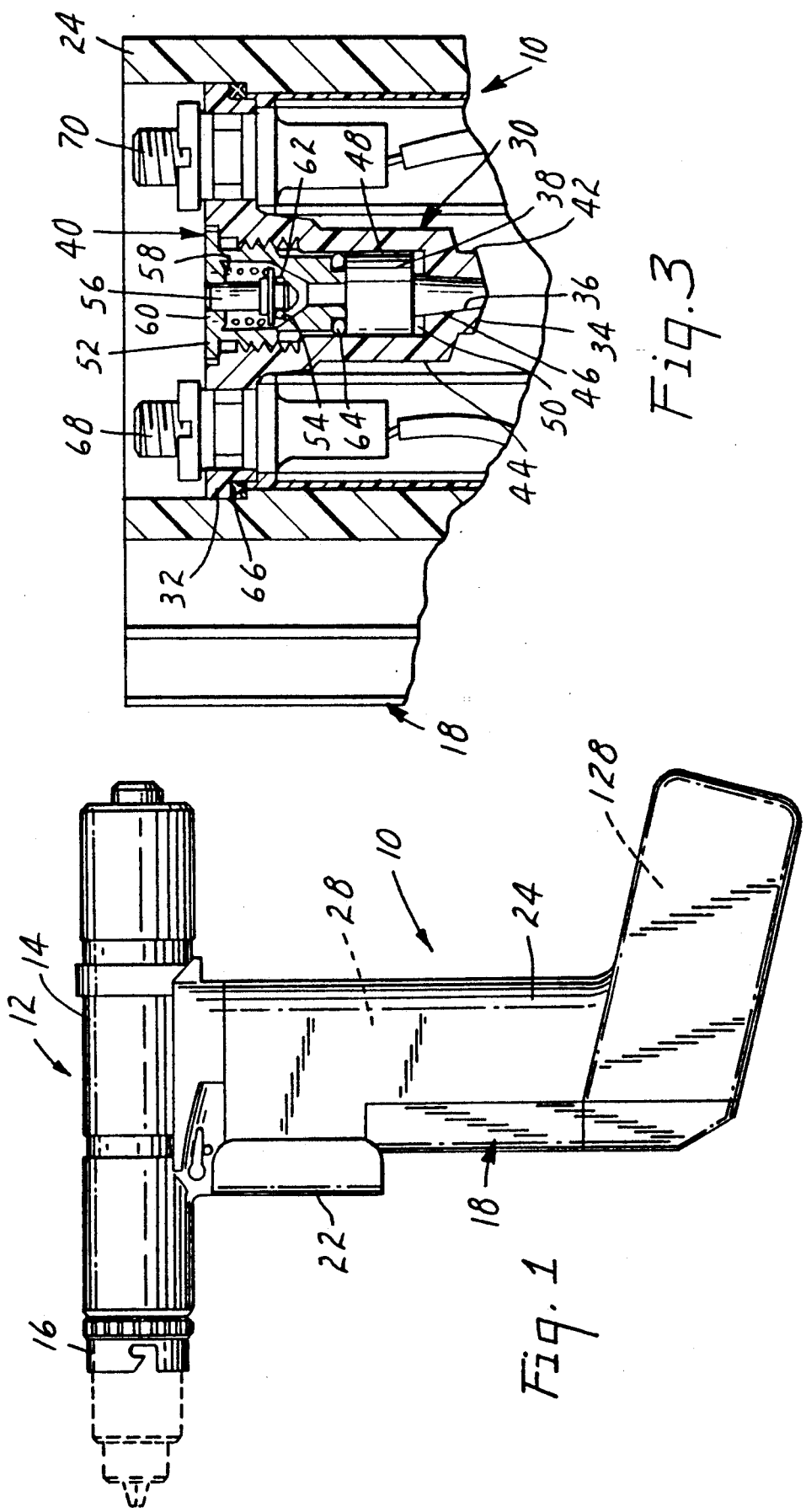
FIG. 1 is a left side elevation of a cordless battery-powered drive assembly of the invention, including a battery housed within the handle of the drive assembly.

Now referring to the drawings, a battery of the present invention is designated in its entirety by the reference numeral 10. The battery 10 is adapted to be repeatedly heat and/or steam sterilized, e.g., in an autoclave, and used in various different orientations, with minimal loss of electrolyte. The battery 10 is particularly designed for powering a drive assembly 12 of the type used to drive orthopedic or other surgical instruments (not shown) during surgery, although other uses are contemplated. Such a drive assembly 12 is typically used in many different orientations and sterilized between operations.

The drive assembly 12 comprises a D.C. electric motor 14 for driving surgical instruments (not shown), and suitable connecting means, such as indicated at 16, for holding surgical instruments in operative engagement with the electric motor 14. The motor 14 may be of the type described in coassigned U.S. Pat. No. 4,728,876, which is incorporated herein by reference. The drive assembly 12 also includes a handle 18 connected to the electric motor 14. The handle 18 preferably includes the battery 10, and manually actuated means (e.g., trigger or switch 22) for controlling the electric motor 14. The handle 18 is preferably releasably engageable with the motor 14.

The battery 10 is preferably of the silver/zinc type containing caustic electrolyte, such as potassium hydroxide in water. One such battery is described in coassigned U.S. Pat. No. 4,892,794, which is incorporated herein by reference.

Figure 2:
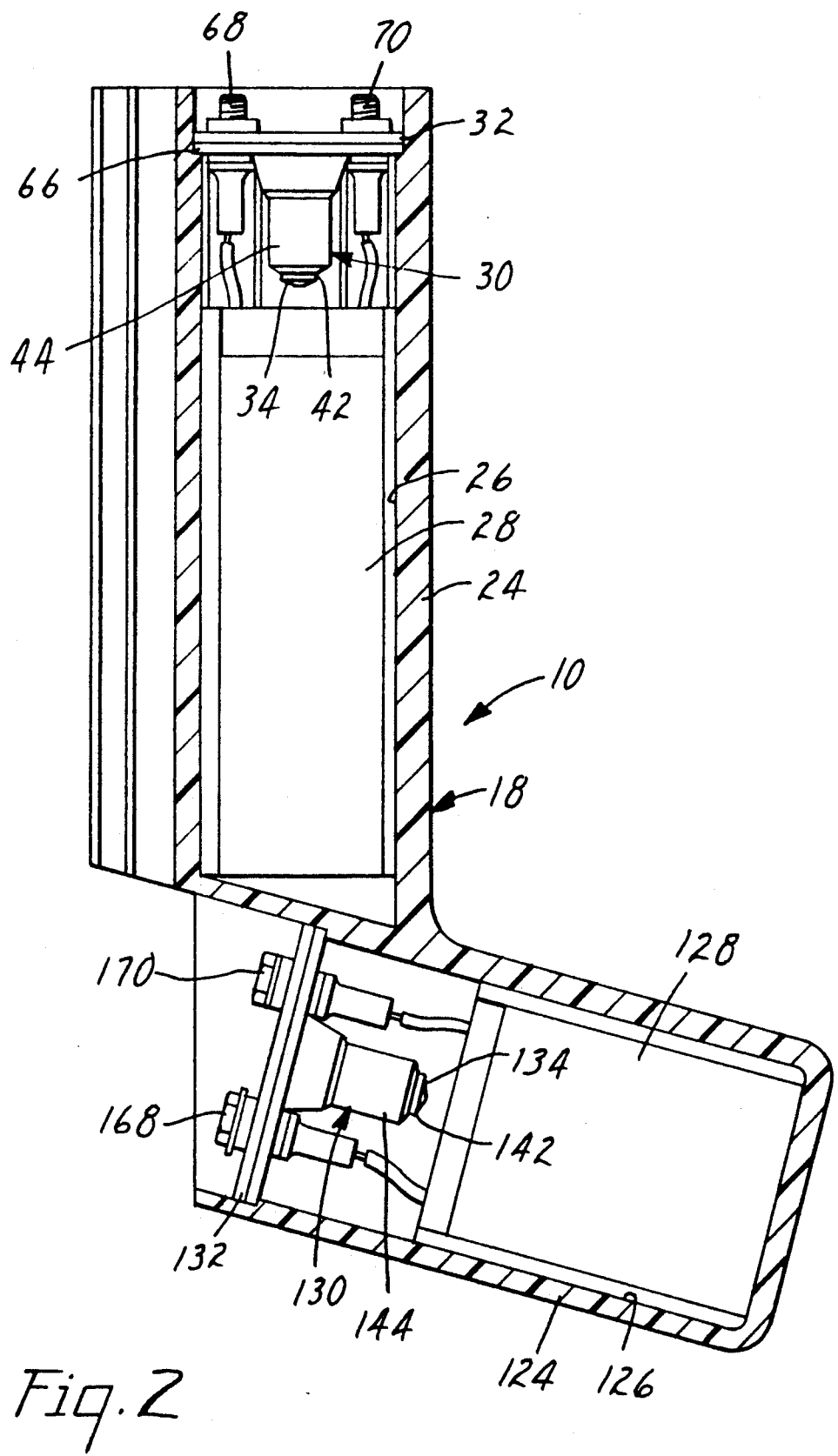
FIG. 2 is an enlarged cross-sectional view substantially along a plane dividing the battery of FIG. 1 into two substantially symmetrical portions.

As shown in FIG. 2, the battery 10 generally comprises a casing 24 having walls defining at least one battery cell, but preferably three battery cells. As used herein, the word "cell" refers to the cavity defined by interior walls of the casing 24. For example, two battery cells 26 and 126 are illustrated in FIG. 2, and a third cell (not shown) is substantially similar to cells 26 and 126 and is positioned immediately adjacent cell 126. Cell 26 is hereafter used to illustrate various aspects of the invention, it being understood that the following discussion also applies to the other battery cells. Parts of cell 126 designated by three digit numbers beginning with "1" indicate parts similar to those designated by the same number as the last two digits in cell 26.

The battery cell 26 has a generally hexahedronic configuration with rounded corners as defined by the walls of the casing 24. The battery 10 includes aqueous fluid electrolyte in the cell 26, and an electrode assembly 28 in the cell 26 including cooperating positive and negative electrodes (also at 28) normally immersed in the electrolyte.

The battery 10 also includes a vent tower 30 extending inwardly from the cell cover 32 of the casing 24 into the cell 26 and terminating at a free end 34 within the cell 26. As used herein, the direction 'inwardly' refers to the direction along the longitudinal axis of the vent tower 30 toward the center of the cell 26, and the direction "outwardly" refers to the opposite direction, that is, the direction along the longitudinal axis of the vent tower 30 toward the outside of the battery casing 24. In FIG. 3, "inwardly" refers to the downward direction, and "outwardly" refers to the upward direction.

The vent tower 30 is provided with a passageway 36 opening inwardly through the free end 34 of the vent tower 30 and opening outwardly through the cell cover 32 for venting gases and pressure from the cell 26. The vent tower 30 includes a porous, hydrophobic filter 38 in the passageway 36 adjacent the free end 34 of the vent tower 30, and pressure-relief means (e.g., valve 40) in the passageway 36 outwardly of the filter 38. The filter 38 permits movement of gas through the passageway 36 while restricting movement of electrolyte through the passageway 36. The pressure-relief valve 40 allows gas in the cell 26 above a predetermined pressure to escape through the passageway 36 while sealing the passageway 36 against the escape of gas below the predetermined pressure.

The free end 34 of the vent tower 30 is spaced sufficiently from any wall defining the battery cell 26 that any void defined by a horizontal plane along the free end 34 of the vent tower 30 and the walls of the casing 24 below the horizontal plane is greater than the volume of free electrolyte regardless of the orientation of the battery 10. As used herein, "horizontal" relates to a plane that is perpendicular to the direction of the force of gravity. "Free" electrolyte refers to electrolyte that is not absorbed in the electrode assembly 28 and which is free to move within the battery cell 26.

For example, if the battery 10 is positioned upside down so that the vent tower 30 extends vertically upwardly from the casing 24, the volume of free electrolyte is less than the volume of the open space that is of lower elevation than the free end 34 of the vent tower 30. And, if the battery 10 is positioned along its side so that the vent tower 30 extends horizontally from the casing 24, the open space that is lower than the elevation of the free end 34 of the vent tower is still greater than the volume of free electrolyte. As a result, the only way that electrolyte can reach the free end 34 of the vent tower 30 is when electrolyte is sloshed around during rapid movement of the battery 10. Electrolyte will not reach the free end 34 of the vent tower 30 while the battery 10 is being heat sterilized, regardless of how the battery 10 is placed in an autoclave.

The free end 34 of the vent tower 30 is preferably configured so as to facilitate movement of electrolyte away from the passageway 36. For example, the free end 34 of the vent tower 30 may have a generally conical, frustoconical or hemispherical configuration with the surface of the free end 34 generally sloping away from the passageway 36 to facilitate movement of electrolyte away from the passageway 36. Most preferably, the surface of the free end 34 is generally frustoconical, forming an included angle of approximately 150 degrees between opposite surfaces of the end 34. The portion 42 of the vent tower 30 immediately adjacent the frustoconical free end 34 may be generally cylindrical and of reduced diameter relative to the main cylindrical portion 44 of the vent tower 30. The shoulder formed between portions 42 and 44 of the vent tower 30 is also preferably tapered or frustoconical.

The filter 38 has an inner end portion 46 in the passageway 36 adjacent the free end 34 of the vent tower 30, and the end surface of the inner end 46 is preferably configured to facilitate movement of electrolyte away from the passageway 36. For example, the inner end portion 46 may also have a generally conical, frustoconical or hemispherical end surface extending slightly outwardly from the free end 34 of the vent tower 30 to facilitate movement of electrolyte away from the passageway 36. The inner end surface of the filter 38 most preferably has a convex configuration with a spherical radius forming a smooth transition relative to the frustoconical surface of the free end 34 of the vent tower 30, although the inner end surface of the filter 38 may alternatively extend slightly beyond the free end 34 of the vent tower 30.

The material of the filter 38 should be chemically resistant to the electrolyte (e.g., 45% KOH/55% $H_2O$), able to withstand temperatures up to 130 degrees Celsius, and have a low surface energy (e.g., an apparent surface energy below 40 dynes/cm). The filter 38 must have a porosity at least sufficient to permit passage of gas generated during charging of the battery 10 so as to prevent the build up of excessive pressure in the cell 26. For example, the average pore size of a PTFE filter 38 may be approximately 10-40 micrometers, with a 40-50 percent void volume.

For example, the filter 38 may be formed of a porous, hydrophobic polymeric material containing fluorine, preferably about 59-76 percent fluorine by weight. Suitable polymeric materials include polytetrafluoroethylene (PTFE) or polyvinylidene fluoride, although other generally hydrophobic materials, such as polypropylene and poly(4-methyl)pentene, are also contemplated.

Most preferably, the filter 38 is molded of porous polytetrafluoroethylene (PTFE) material, such as the PTFE material sold under the trade designation "POREX IRM0217 PTFE" by the Porex Technologies Corporation of Fairburn, Ga. This material has pore sizes of 18-30 micrometers, a 40-50 percent void volume, and permits an air flow through the filter 38 of at least 10ml/minute with an inlet pressure of 4.9 inches (125mm) water.

When this PTFE material was tested to determine its "apparent" surface energy in accordance with a modification of the test described in U.S. Pat. No. 4,892,794 (incorporated herein by reference), the apparent surface energy was found to be approximately 26-27 dynes/cm. That is, the sample repelled a single drop of hexadecane having a surface tension of 27.3 dynes/cm, but wicked in tetradecane having a surface tension of 26.4 dynes/cm. The modified test preferably consists of gently placing a single drop of the test liquids on a level, flat surface of each of five or more samples to determine which liquids are repelled or wicked in the test samples. This test is performed at ambient temperature (23-25 degrees Celsius) and ambient pressure (about 101kPa), and the sample is observed for thirty seconds.

Alternative materials also include the polyvinylidene fluoride material sold under the trade designation "KYNAR" by Pennwalt Corporation of Philadelphia, Pa. The "KYNAR" brand material is believed to have an apparent surface energy of 30-40 dynes/cm. In any case, the filter material should be sufficiently hydrophobic to repel solutions of methanol and water having more than 21 percent methanol by volume under ambient conditions, although it is most preferred that the material be hydrophobic enough to repel such solutions having at least 65 percent methanol (e.g., an apparent surface energy of less than 30 dynes/cm).

The filter 38 preferably has an outer end portion 48 having a larger cross-sectional area than the inner end portion 46 of the filter 38, and a shoulder formed along a surface of the filter 38 between the inner end portion 46 and the outer end portion 48 of the filter 38. The inner end portion 46 of the filter 38 is tapered from the shoulder to its end surface, and the passageway 36 of the vent tower 30 has a configuration complementary to the configuration of the filter 38.

Most preferably, the outer end portion 48 of the filter 38 is generally cylindrical, and the inner end portion 46 of the filter 38 is generally conical or frustoconical, with the diameter of the inner end portion 46 across the passageway 36 being approximately twenty percent smaller along its end surface than adjacent the outer end portion 48 of the filter 38. The inner end portion 46 of the filter 38 is force or interference fit within the passageway 36 of the vent tower 30 in order to prevent electrolyte from seeping through the passageway 36 between the filter 38 and the walls of the passageway 36. Alternatively, a sealant or gasket (not shown) may be provided for sealing between the inner end portion 46 of the filter 38 and the walls of the passageway 36, although the interference fit is preferred.

The cross-sectional diameter of the inner end portion 46 across the passageway 36 is preferably approximately 35-50 percent smaller than the cross-sectional diameter of the outer end portion 48 across the passageway 36. While the outer end portion 48 is closely received in the passageway 36, it is not subjected to the tight interference fit of the inner end portion 46.

An annular filter seal 50 may be provided between the shoulder of the filter 38 and a ledge formed in the passageway 36 to seal between the filter 38 and the passageway 36. The filter seal 50 may conveniently be formed of an elastomeric material, such as ethylene-propylene rubber having a Shore A durometer of 30-45, and preferably functions both as a seal and a cushion. The cross section of the filter seal 50 is preferably generally rectangular to completely fill any space between the filter's shoulder and the ledge of the passageway 36.

The pressure-relief valve 40 comprises a generally cylindrical valve housing 52 mounted in the vent tower 30 (or casing 24), for example, by a threaded connection along the circumference of the valve housing 52. The valve housing 52 has a tapered valve seat 54 defining a portion of the passageway 36 through the vent tower 30, and a poppet 56 is movable within the passageway 36 relative to the valve seat 54 between a sealing position wherein the poppet 56 seals against the valve seat 54 and a pressure-relief position wherein the poppet 56 is spaced from the valve seat 54 so as not to seal against the valve seat 54. The valve seat 54 may be tapered at an included angle of approximately 60 degrees. The poppet 56 preferably includes a shaft portion extending outwardly from a tip portion and having a smaller diameter than its inward tip portion.

A resilient spring means, such as a coil spring 58, is provided for biasing the poppet 56 against the valve seat 54. The spring 58 is sufficiently stiff to prevent the escape of gas below the predetermined "release" pressure, e.g., below approximately 17 psig (220kPa), outwardly through the passageway 36 and sufficiently flexible to allow the escape of gas above the predetermined pressure outwardly through the passageway 36. The spring 58 is preferably positioned around the shaft portion of the poppet 56, with one end of the spring 58 acting against the tip of the poppet 56, and the other end of the spring acting against a vent nut 60 that is threadably received in the outward end of the valve housing 52.

The release pressure at which gas is permitted to escape could be set at about 35 psig (340kPa), which is believed to be high enough to prevent the escape of gas during sterilization in an autoclave. A 35 psig release pressure requires that extra care be taken to ensure that the casing 24 of the battery 10 is strong enough to withstand the pressure. The release pressure of the valve 40 is preferably set higher than 15 psig (205kPa) so that the escape of gas is prevented when the battery 10 is placed in a very low pressure environment, such as during air transport. For certain uses, the release pressure could be set at a relatively low pressure, such as 4 psig (130kPa), although this is not preferred in the context of batteries used to power orthopedic or other surgical instruments.

The vent nut 60 preferably includes an opening designed to slidably receive the shaft portion of the poppet 56 to guide the poppet 56, and additional openings or other means to allow the passage of gas being vented from the battery cell 26. For example, the vent nut 60 may include one opening with a guide portion adapted for closely and slidably receiving the shaft of the poppet 56 and one or more vent portions adapted to permit the passage of vented gas.

The vent nut 60 also provides a means for adjusting the spring 58 to control the pressure at which gas is allowed to escape through the passageway 36. By turning the vent nut 60 inwardly, the spring 58 is compressed and the minimum pressure at which gas is allowed to escape through the passageway 36 is increased. The adjustability of the vent nut 60 may be used during assembly of the battery 10 to permanently set the release pressure of the pressure-relief valve 40. For example, if the battery 10 is being used with a vibrating drive assembly 12, such as an assembly 12 for driving a drill or saw blade, a punch, soldering iron or other suitable means may be used to lock the vent nut 60 in its adjusted position after the release pressure is set.

An elastomeric valve seal 62 is preferably mounted on the inward tip of the poppet 56 for sealing between the valve seat 54 and the poppet 56. The valve seal 62 may conveniently take the form of an O-ring seal 62 of an elastomeric material such as ethylene-propylene rubber. The inward tip of the poppet 56 preferably has a generally conical or frustoconical configuration that is complementary to the configuration of the valve seat 54, and the tip includes a channel configured for receiving and retaining the valve seal 62.

The inner end of the valve housing 52 preferably includes a reduced diameter portion extending inwardly from the body of the valve housing 52 for receiving a valve-housing/filter seal 64, and a shoulder between the reduced diameter portion and the body of the housing 52 for compressing the valve-housing/filter seal 64 against the outer surface of filter 38 adjacent its periphery. The valve-housing/filter seal 64 is formed of an elastomeric material, such as ethylene-propylene rubber having a Shore A durometer of approximately 70. The valve-housing/filter seal 64 may be an O-ring seal having a cross-sectional diameter appropriate for sealing between the reduced diameter portion of the valve housing 52 and the walls of the vent tower 30.

The cell cover 32 and vent tower 30 are preferably integrally formed of a non-porous material, such as polysulfone material filled with glass (e.g., ten to twenty percent glass by weight). Suitable polysulfone materials include the material sold under the trade designation "UDEL GF-110" by the Amoco Corporation of Chicago, Il. The cell cover 32 conveniently forms one wall of the battery cell 26, and has a generally rectangular configuration.

A ledge or channel is formed along the periphery of the cell cover 32 for receiving a gasket 66 for sealing between the cover 32 and the other walls of the casing 24. The gasket 66 preferably is formed of elastomeric material, and is in the form of a "quad-ring" molded in a suitable rectangular configuration. The "quad-ring" gasket 66 has a generally X-shaped cross section when uncompressed.

The cell cover 32 also includes openings adapted to receive the battery terminals 68 and 70, which are preferably arranged generally adjacent opposite ends of the cell cover 32. The vent tower 30 preferably extends from a central portion of the cell cover 32 between the terminals 68 and 70, thereby separating the terminals 68 and 70 and their associated wiring from one another. Most preferably, the vent tower 30 extends from the center of the cell cover 32 so that the free end 34 of the vent tower 30 is equally spaced from the opposite side walls of the battery casing 24.

The vent tower 30 will now be described in reference to a specific battery cell 26 used in an orthopedic or surgical instrument to further illustrate various details by way of example. The total internal volume of the cell of the example is 53ml, and it contains a total volume of electrolyte of approximately 20ml, including free electrolyte having a total volume of 4ml. The vent tower 30 of this example has an overall length of approximately 20mm as measured from the inner surface of the cell cover 32 to the free end 34, and can accommodate at least 7ml free electrolyte when the battery 10 is positioned upside down (i.e., with the vent tower 30 extending upwardly from the cell cover 32) without submerging the free end 34 of the vent tower 30.

The vent towers 30, 130 each preferably have an overall length within the range of 10-25mm as measured from the inner surface of the cell cover 32, 132 (e.g., the vent tower 130 may have a length of approximately 16mm, while the vent tower 30 may have a length of approximately 20mm).

Most preferably, the filter 38 of this example would have a thickness longitudinally along the passageway 36 of approximately 10-20mm (e.g., 14mm), and the pressure-relief valve 38 is positioned within the passageway 36 outwardly of the filter 38. The outer end portion 48 of the filter 38 has a cross-sectional area across the passageway of approximately 28-50mm$^2$ (e.g., 36mm$^2$), and the inner end portion 46 has a cross-sectional area across the passageway 36 of approximately 3-13mm$^2$ (e.g., 5-8mm$^2$). The end surface of the inner end portion 46 of the filter 38 is convex and has a radius of approximately 2-4mm (e.g., 2.3mm).

As various changes could be made in the above constructions without departing from the scope of the invention, it is intended that all matter contained in the above description or shown in the accompanying drawing be interpreted as illustrative and not in a limiting sense.

We claim:

1. A battery comprising a casing having walls defining at least one battery cell, aqueous fluid electrolyte in the cell, an electrode assembly in the cell including positive and negative electrodes normally immersed in the electrolyte, and a vent tower extending inwardly from a wall of the casing into the cell and terminating at a free end, the vent tower having:

a passageway opening inwardly through the free end of the vent tower and opening outwardly through the casing for venting gases and pressure from the cell;

a porous, hydrophobic filter in the passageway adjacent the free end of the vent tower permitting movement of gas through the passageway while restricting movement of liquid through the passageway; and pressure-relief means in the passageway for allowing gas in the cell above a predetermined pressure to escape through the passageway while sealing the passageway against the escape of gas below the predetermined pressure;

the free end of the vent tower being spaced sufficiently from any wall defining the battery cell that any void defined by a horizontal plane along the free end of the vent tower and the walls of the casing below the horizontal plane is greater than the volume of free electrolyte regardless of the orientation of the battery.

2. A battery according to claim 1 wherein the free end of the vent tower is configured so as to facilitate movement of electrolyte away from the passageway.

3. A battery according to claim 2 wherein the free end of the vent tower has a generally conical, frustoconical or hemispherical configuration with the surface of the free end generally sloping away from the passageway to facilitate movement of electrolyte away from the passageway.

4. A battery according to claim 3 wherein the filter has an inner end portion adjacent the free end of the vent tower, the inner end portion having a generally conical, frustoconical or hemispherical end surface extending slightly outwardly from the free end of the vent tower to facilitate movement of electrolyte away from the passageway.

5. A battery according to claim 4 wherein the filter has an outer end portion having a larger cross-sectional area than the inner end portion of the filter, and a shoulder formed along a surface of the filter between the inner end portion and the outer end portion of the filter, the inner end portion of the filter being tapered from the shoulder to its end surface, and the passageway of the vent tower having a configuration complementary to the configuration of the inner and outer end portions and shoulder of the filter, the vent tower further comprising an elastomeric filter seal positioned along the shoulder of the filter for sealing between the filter and the passageway.

6. A battery according to claim 5 wherein the outer end portion of the filter is generally cylindrical, and the inner end portion of the filter is generally conical or frustoconical, the cross-sectional area of the inner end portion across the passageway being approximately twenty percent smaller along its end surface than adjacent the outer end portion of the filter, the inner end portion of the filter being force fit within the passageway of the vent tower, and the cross-sectional area of the inner end portion across the passageway being approximately 35-50 percent smaller than the cross-sectional area of the outer end portion across the passageway.

7. A battery according to claim 5 wherein the pressure-relief means comprises:
 a valve housing mounted in the vent tower or casing having a tapered valve seat defining a portion of the passageway through the vent tower;
 a poppet movable within the passageway relative to the valve seat between a sealing position wherein the poppet seals against the valve seat and a pressure-relief position wherein the poppet does not seal against the valve seat;
 resilient spring means for biasing the poppet against the valve seat, the resilient spring means being sufficiently stiff to prevent the escape of gas below the predetermined pressure outwardly through the passageway and sufficiently flexible to allow the escape of gas above the predetermined pressure outwardly through the passageway; and
 an elastomeric valve-housing/filter seal for sealing between the valve housing and filter along the walls of the passageway.

8. A battery according to claim 3 wherein the filter is formed of a porous, hydrophobic polymeric material containing fluorine.

9. A battery according to claim 8 wherein the filter is formed of porous polytetrafluoroethylene material.

10. A battery according to claim 9 wherein the filter is formed of porous polytetrafluoroethylene material having an average pore size of approximately 10-40 micrometers, the filter having a porosity at least sufficient to permit passage of gas generated during charging of the battery.

11. A battery-powered drive assembly for driving surgical instruments in various orientations without leakage during operation or sterilization, the drive assembly comprising an electric motor for driving surgical instruments, connecting means for holding surgical instruments in operative engagement with the electric motor, and a handle connected to the electric motor; the handle including manually actuated means for controlling the electric motor, and a battery comprising a casing having walls defining at least one battery cell, aqueous fluid electrolyte in the cell, an electrode assembly in the cell including positive and negative electrodes normally immersed in the electrolyte, and a vent tower extending inwardly from a wall of the casing into the cell and terminating at a free end, the vent tower having:
 a passageway opening inwardly through the free end of the vent tower and opening outwardly through the casing for venting gases and pressure from the cell;
 a porous, hydrophobic filter in the passageway adjacent the free end of the vent tower permitting movement of gas through the passageway while restricting movement of liquid through the passageway; and
 pressure-relief means in the passageway for allowing gas in the cell above a predetermined pressure to escape through the passageway while sealing the passageway against the escape of gas below the predetermined pressure;
 the free end of the vent tower being spaced sufficiently from any wall defining the battery cell that any void defined by a horizontal plane along the free end of the vent tower and the walls of the casing below the horizontal plane is greater than the volume of free electrolyte regardless of the orientation of the battery.

12. A drive assembly according to claim 11 wherein the free end of the vent tower is configured so as to facilitate movement of electrolyte away from the passageway.

13. A drive assembly according to claim 12 wherein the free end of the vent tower has a generally conical, frustoconical or hemispherical configuration with the surface of the free end generally sloping away from the passageway to facilitate movement of electrolyte away from the passageway, the filter having an inner end portion adjacent the free end of the vent tower, the inner end portion having a generally conical, frustoconical or hemispherical end surface extending slightly outwardly from the free end of the vent tower to facilitate movement of electrolyte away from the passageway.

14. A drive assembly according to claim 13 wherein the filter has an outer end portion having a larger cross-sectional area than the inner end portion of the filter, and a shoulder formed along a surface of the filter between the inner end portion and the outer end portion of the filter, the inner end portion of the filter being tapered from the shoulder to its end surface, and the passageway of the vent tower having a configuration complementary to the configuration of the inner and outer end portions and shoulder of the filter, the vent tower further comprising an elastomeric filter seal positioned along the shoulder of the filter for sealing between the filter and the passageway.

15. A drive assembly according to claim 14 wherein the outer end portion of the filter is generally cylindrical, and the inner end portion of the filter is generally conical or frustoconical, the cross-sectional area of the inner end portion across the passageway being approximately twenty percent smaller along its end surface than adjacent the outer end portion of the filter, the inner end portion of the filter being force fit within the passageway of the vent tower, and the cross-sectional area of the inner end portion across the passageway being approximately 35-50 percent smaller than the cross-sectional area of the outer end portion across the passageway.

16. A drive assembly according to claim 15 wherein the pressure-relief means comprises:

a valve housing mounted in the vent tower or casing having a tapered valve seat defining a portion of the passageway through the vent tower;

a poppet movable within the passageway relative to the valve seat between a sealing position wherein the poppet seals against the valve seat and a pressure-relief position wherein the poppet does not seal against the valve seat;

resilient spring means for biasing the poppet against the valve seat, the resilient spring means being sufficiently stiff to prevent the escape of gas below the predetermined pressure outwardly through the passageway and sufficiently flexible to allow the escape of gas above the predetermined pressure outwardly through the passageway; and an elastomeric valve-housing/filter seal for sealing between the valve housing and filter along the walls of the passageway.

17. A drive assembly according to claim 15 wherein the filter is formed of a porous, hydrophobic polymeric material containing fluorine.

18. A drive assembly according to claim 17 wherein the filter is formed of porous polytetrafluoroethylene material.

19. A drive assembly according to claim 18 wherein the filter is formed of porous polytetrafluoroethylene material having an average pore size of approximately 10-40 micrometers, the filter having a porosity at least sufficient to permit passage of gas generated during charging of the battery.

20. A drive assembly according to claim 19 wherein the casing includes a cell cover defining one wall of the cell and an elastomeric seal for sealing between the cell cover and other walls of the casing, the vent tower extending inwardly into the cell from the cell cover, the cell cover and vent tower being integrally formed of polysulfone material filled with glass; the filter having a thickness longitudinally along the passageway of approximately 10-20mm, and the pressure-relief means is positioned within the passageway outwardly of the filter, the outer end portion of the filter having a cross-sectional area across the passageway of approximately 28-50mm$^2$, the inner end portion having a cross-sectional area across the passageway of approximately 3-13mm$^2$, and the end surface of the inner end portion being convex and having a radius of approximately 2-4mm; and the pressure-relief means comprising:

a valve housing mounted in the vent tower or casing having a tapered valve seat defining a portion of the passageway through the vent tower;

a poppet movable within the passageway relative to the valve seat between a sealing position wherein the poppet seals against the valve seat and a pressure-relief position wherein the poppet does not seal against the valve seat;

resilient spring means for biasing the poppet against the valve seat, the resilient spring means being sufficiently stiff to prevent the escape of gas below the predetermined pressure outwardly through the passageway and sufficiently flexible to allow the escape of gas above the predetermined pressure outwardly through the passageway; and an elastomeric valve-housing/filter seal for sealing between the valve housing and filter along the walls of the passageway.

* * * * *

UNITED STATES PATENT AND TRADEMARK OFFICE
CERTIFICATE OF CORRECTION

PATENT NO. : 5,080,983

DATED : January 14, 1992

INVENTOR(S) : Charles E. Alexson, Matthew T. Scholz and Robert P. Zaspel

It is certified that error appears in the above-identified patent and that said Letters Patent is hereby corrected as shown below:

ON THE TITLE PAGE

On the Title page, and item [19], "Alexon" should read --Alexson--.

Signed and Sealed this

Thirty-first Day of August, 1993

*Attest:*

BRUCE LEHMAN

*Attesting Officer*     *Commissioner of Patents and Trademarks*